(12) United States Patent
Scecina et al.

(10) Patent No.: US 6,741,876 B1
(45) Date of Patent: May 25, 2004

(54) METHOD FOR DETERMINATION OF ANALYTES USING NIR, ADJACENT VISIBLE SPECTRUM AND DISCRETE NIR WAVELENTHS

(75) Inventors: Thomas Scecina, Medfield, MA (US); Romauld Pawluczyk, Conestogo (CA); Theodore E. Cadell, Conestogo (CA)

(73) Assignee: CME Telemetrix Inc., Waterloo (CA)

( * ) Notice: Subject to any disclaimer, the term of this patent is extended or adjusted under 35 U.S.C. 154(b) by 0 days.

(21) Appl. No.: 10/070,187
(22) PCT Filed: Aug. 31, 2000
(86) PCT No.: PCT/CA00/01000
§ 371 (c)(1), (2), (4) Date: Jun. 28, 2002
(87) PCT Pub. No.: WO01/16577
PCT Pub. Date: Mar. 8, 2001

(51) Int. Cl.⁷ .................................................. A61B 5/00
(52) U.S. Cl. .................................... 600/316; 600/322
(58) Field of Search ................................ 600/310, 316, 600/322, 323, 473; 356/39, 300, 319, 320, 326, 328; 250/339.01, 339.02, 339.05, 339.06, 339.07, 339.11, 339.12, 340, 341.1, 341.2, 341.8

(56) References Cited

U.S. PATENT DOCUMENTS

| | | |
|---|---|---|
| 4,655,225 A | 4/1987 | Dahne et al. |
| 4,882,492 A | 11/1989 | Schlager |
| 4,883,953 A | 11/1989 | Koashi et al. |
| 4,915,827 A | 4/1990 | Rosenthal |
| 4,975,581 A | 12/1990 | Robinson et al. |
| 5,028,787 A | 7/1991 | Rosenthal |
| 5,077,476 A | 12/1991 | Rosenthal |
| 5,237,178 A | 8/1993 | Rosenthal et al. |
| 5,319,200 A | 6/1994 | Rosenthal et al. |
| 5,361,758 A | 11/1994 | Hall et al. |
| 5,438,201 A | 8/1995 | Rosenthal et al. |
| 5,830,132 A | * 11/1998 | Robinson .................... 600/310 |

* cited by examiner

Primary Examiner—Eric F. Winakur
(74) Attorney, Agent, or Firm—Hovey Williams LLP (57) ABSTRACT

Described is a method for measuring the concentration of a blood constituent within a body part (80) of a living subject which comprises irradiating a body part of the subject with a continuum of a broad spectrum of radiation in adjacent and near infrared range of the electomagnetic spectrum; collecting the band of radiation after the radiation has been directed onto the part; dispersing the continuum of collected radiation into a dispersed spectrum of component wavelengths onto a detector (120) the detector taking measurements of at least one of transmitted or reflected radiation from the collected radiation; and transferring the measurements to a processor (300), and then measuring the same kind of absorbance or reflectance with respect to one or more a discrete wavelengths of radiation from the longer near infrared range and using the measurements to calculate the concentration of the constituent.

38 Claims, 4 Drawing Sheets

METHOD FOR DETERMINATION OF ANALYTES USING NIR, ADJACENT VISIBLE SPECTRUM AND DISCRETE NIR WAVELENTHS

FIELD OF INVENTION

This invention relates to a non-invasive device and method for monitoring concentration levels of blood constituents in living subjects such as humans or animals, using a full spectrum of the near infrared portion of the light spectrum and adjacent visible spectrum in addition to discrete longer wavelengths of the near infrared region of the light spectrum.

BACKGROUND OF INVENTION

1. Invasive Techniques

Invasive techniques of measuring blood constituents are in common usage. These techniques are painful, potentially dangerous and expensive to operate. A typical procedure is to obtain a blood sample from a vein and this sample is then tested in a medical laboratory, using a number of chemical procedures to measure each constituent separately. Alternatively, home glucose testing uses a finger puncture that is spotted onto an enzyme-based semi-permeable membrane test strip and is allowed to react for a certain length of time, with insulin administration then based upon either a visual colour comparison with a standard colour chart or by means of a more accurate and unambiguous spectroscopic technique (for example reflectance). There is a risk of infection and sometimes a patient can develop a rash when these invasive techniques are used.

2. Non-Invasive Techniques

Previous devices for non-invasively monitoring concentration of blood constituents of a patient are known. Usually, a sensor is used to externally measure either the concentration of the constituent in gases emitted by the body; the concentration contained in perspiration; or the concentration contained in body fluids such as tears, saliva or urine samples. An example of this approach is the GlucoWatch, developed by Cygnus. It draws interstitial fluid from a body part onto a patch and measures the glucose in that fluid. This approach is not ideal in that the patch causes irritation and each patch, which last for 12 hours, needs to be calibrated using a reference method which requires an invasive finger stick to obtain a blood sample. Alternatively, the blood constituent is measured using radiation passed through a part of the patient's body such as the earlobe or reflected from a body part such as a finger or forearm. However, of the previous radiation devices, some have a radiation source which emits light in one wavelength only or two wavelengths (see for example U.S. Pat. No. 4,655,225; U.S. Pat. No. 4,883,953; and U.S. Pat. No. 4,882,492); other previous devices have more than one light source but have only a limited number of measuring wavelengths (U.S. Pat. Nos. 4,915,827; 5,028,787; 5,077,476; 5,237,178; 5,319,200 and 5,438,201)].

Some of these previous devices have had a number of discrete wavelength sources obtained through use of a broad-band lamp whose light is optically coupled through a number of light filters, each with its own designated transmission wavelength, to the test sample.

Further, some previous devices are controlled to take a series of measurements at successively higher or lower wavelengths. This can be extremely time consuming.

Other techniques have included those which measure a full spectrum of absorptions, with a large number (for example, 128 or 256) of wavelengths in a specific range and those that measure a limited number of wavelengths. Those that measure full spectra typically use the wavelengths in the 580 to 1100nm range (see for examples U.S. Pat. No. 5,361,758 and U.S. Pat. No. 4,975,581). An advantage of full spectra measurements is that they provide information about the desired analyte as well as information about interfering substances (e.g., other analytes) and effects (e.g., light scattering).

Some of the methods that measure a limited number of wavelengths utilize the 1100 to 1700 nm region because of sharper analyte spectra that exist in this region. Others measure at wavelengths in the 600 to 1100 nm region. These methods provide information relating to the analyte of interest, but fail to provide sufficient independent information about other analytes whose absorption interferes with the desired analyte.

Some previous devices which take measurements in earlobes do not take into account changes in the thickness of a patient's earlobes compared to that of other patients or the change in size of a patient's earlobes or the change in the transmission path length due to the pulsing of blood through the patient; or, they do not take into account temperature variations in the earlobes from patient to patient, or, the results fluctuate with prolonged operation.

Overall, previous non-invasive devices and techniques have not been sufficiently accurate to be used in place of invasive techniques in the measurement of blood constituent concentration levels by patients; or they have been designed to measure one component only and must be physically changed to measure for a different component; or, the devices take an unreasonably long time to produce a result; or, they cannot produce results in an easy-to-use form; or, they cannot measure the results of two or more constituents simultaneously. Obviously, if the device gives an inaccurate reading, disastrous results could occur for the patient using the device to calculate, for example, dosages for insulin administration.

SUMMARY OF THE INVENTION

The present invention provides a method for monitoring the concentration level of a particular constituent or, alternatively, of measuring the concentration level of more than one different constituents in a non-invasive device, the method producing result(s) in a short time period that is/are accurate and reliable.

The present inventors have determined that measurement at a continuum of wavelengths from 500 to 1100 nm provides information about the concentration of the desired analyte and very importantly further information about the many other analytes that interfere with an accurate measurement. The inventors have discovered that analyte measurement accuracy is enhanced by adding a limited number of discrete wavelength measurements in the 1100 to 1700 nm region to a full spectra absorption measurement of a continuum of wavelengths in the 500 to 1000 nm region. Using this combination it is possible to gain a significant improvement in analyte measurement accuracy. As used herein the 500–1100 nm region is referred to as the "AV and NIR region" while the 1100–1700 nm region is referred to as the "longer wavelength NIR region" or "LWNIR".

According to preferred embodiments, in each case measurement of discrete wavelengths is at a sufficiently high signal to noise ratio in order to achieve desired results.

Accordingly, in its broad aspect, the present invention provides a method for monitoring the concentration level of a constituent in tissue comprising placing the tissue in a non-invasive device capable of emitting radiation; directing the radiation onto the tissue; measuring radiation collected from the tissue; calculating the concentration level based on the measured radiation wherein the radiation directed onto the tissue and collected from the tissue is of a continuum of wavelengths in the 500–1100 nm range, and discrete wavelengths in the range from 1100 to 1700 nm.

According to one aspect the present invention provides a method for measuring concentration levels of blood constituents within a living subject such as humans or animals wherein, in respect of the AV and NIR region, there is used a polychromatic light source or other radiation source that emits a broad spectrum of light in the range from 500 nm to 1100 nm. For this range, the method comprises the steps of directing light at a continuum of wavelengths simultaneously onto a bodypart of a subject; collecting the continuum of light after the light has been directed onto the part; focusing the collected light onto a grating, dispersing the continuum of light into a dispersed spectrum of component wavelengths of the collected light onto a linear array detector, the linear array detector taking measurements of at least one of transmitted and reflected light from the collected light in adjacent visible spectrum, and near infrared range from 500–1100 region, and the measurements are transferred to a microprocessor. With respect to the LWNIR region the method comprises the steps of directing one or more narrow band sources of light on the body part, collecting the one or more narrow bands on one or more detectors (depending on the specific configuration chosen), these measurements are also transferred to the microprocessor. The microprocessor then uses these measurements and a calibration algorithm to calculate the concentration level of said at least one constituent of said blood and tissue.

In another aspect of this invention, there is provided a method for determining a concentration of a constituent in a tissue of a subject comprising the steps of: irradiating the tissue with a broad spectrum of radiation in the AV and NIR region; irradiating the tissue with radiation in the longer wavelength NIR region; measuring at least one of transmitted or reflected radiation from the tissue at a continuum of wavelengths in the AV and NIR region and at one or more discrete wavelengths in the longer wavelength NIR region; and calculating the concentration of the constituent on the basis of the measurements, thereby determining the concentration of the constituent in the tissue.

Preferably, the continuum of wavelengths from the AV and NIR region is between 500 and 1100 nm According to another embodiment, the discrete wavelength in the longer wavelength NIR region is between 1100 and 1700 nm.

According to yet another embodiment, one or more discrete wavelengths are between 1100 and 1300 nm.

According to another embodiment, one or more discrete wavelengths is between 1590 and 1700 nm.

According to another embodiment, at least two discrete wavelengths are measured at least one of which is between 1100 and 1300 nm and at least one of which is between 1590 and 1700 nm.

According to yet another embodiment, the discrete wavelength measurements are at 1150, 1195, 1215, 1230, 1240 and 1250 nm.

According to another embodiment, the discrete wavelength measurements are at 1595, 1610 and 1620 nm.

According to another embodiment, the discrete wavelength measurements are at 1150, 1195, 1215, 1230, 1240, and 1250 nm, and at 1595, 1610 and 1620 nm.

According to yet another embodiment, the radiation at each discrete wavelength is provided by a separate energy source.

According to another embodiment, the radiation at each of the discrete wavelengths is provided sequentially.

According to another embodiment the radiation at all of the discrete wavelengths is provided simultaneously.

According to another embodiment, a single energy source provides continuous energy over the radiation range of 1100 to 1300 nm.

According to another embodiment, there is provided a single energy source provides continuous energy over the radiation range of 1140 to 1260 nm.

According to another embodiment, a single energy source provides radiation in the range of 500 to 1300 nm.

According to another embodiment, the steps of irradiating the tissue in the AV and NIR region, and in the longer wavelength NIR region, are done simultaneously, and the measurement in each of said AV and NIR region and said longer wavelength NIR region is made simultaneously.

In yet other aspect of the present invention, there is provided a method for measuring concentration of a blood constituent within a body part of a living subject comprising:

irradiating a body part of the subject with a broad spectrum of radiation in the AV and NIR region;

collecting the radiation from the AV and NIR region after the radiation has been directed onto the part;

dispersing the collected radiation into a dispersed spectrum of component wavelengths onto a detector, the detector taking measurements of at least one of transmitted and reflected radiation from the collected radiation; transferring the measurements to a processor;

irradiating the body part of the subject with radiation in the longer wavelength NIR region;

detecting one or more discrete wavelengths in the longer wavelength NIR region after the radiation has been directed onto the part, the detector taking measurements of at least one of transmitted and reflected radiation; and transferring the measurements to a processor; based on the measurements and one or more calibration algorithms, the processor calculating the concentration of said constituent of said blood.

According to one embodiment, the detector is a linear array detector and the measurement is of absorbed radiation.

According to another embodiment, the continuum of wavelengths from the AV and NIR region is between 500 and 1100 nm.

According to another embodiment, the discrete wavelength in the longer wavelength NIR region is between 1100 and 1700 nm.

According to another embodiment, the one or more discrete wavelengths are between 1100 and 1300 nm.

According to another embodiment, the one or more discrete wavelengths is between 1590 and 1700 nm.

According to another embodiment, at least two discrete wavelengths are measured at least one of which is between 1100 and 1300 nm and at least one of which is between 1590 and 1700 nm.

According to another embodiment, the discrete wavelength measurements are at 1150, 1195, 1215, 1230, 1240 and 1250 nm.

According to another embodiment, the discrete wavelength measurements are at 1595, 1610 and 1620 nm.

According to another embodiment, the discrete wavelength measurements are at 1150, 1195, 1215, 1230, 1240, and 1250 nm, and at 1595, 1610 and 1620 nm.

In yet another aspect of the present invention, there is provided a method for measuring concentration of a blood constituent within a body part of a living subject comprising:

irradiating the body part of the subject with a first continuum of a broad spectrum band of radiation in the AV and NIR region;

collecting the first band of radiation after the radiation has been directed onto the part;

dispersing the continuum of collected radiation into a dispersed spectrum of component wavelengths onto a detector, the detector taking measurements of at least one of transmitted and reflected radiation from the collected radiation; and transferring the measurements to a processor;

irradiating the body part of the subject with a second continuum of a radiation band in the longer wave NIR region;

collecting the second band of radiation after the radiation has been directed onto the part;

dispersing the continuum of collected radiation into a dispersed spectrum of component wavelengths onto a detector;

detecting one or more discrete wavelengths in the longer wavelength NIR region;

the detector taking measurements of at least one of transmitted and reflected radiation from the collected radiation; and transferring the measurements to a processor based on the measurements and one or more calibration algorithms, the processor calculating the concentration of said constituent of said blood, thereby determining.

According to one embodiment, the detector is a linear array detector and the measurement is of absorbed radiation.

According to another embodiment, the continuum of wavelengths from the AV and NIR region is between 500 and 1100 nm.

According to another embodiment, the discrete wavelength in the longer wavelength NIR region is between 1100 and 1700 nm.

According to another embodiment, the one or more discrete wavelengths are between 1100 and 1300 nm.

According to another embodiment, the one or more discrete wavelengths is between 1590 and 1700 nm.

According to another embodiment, at least two discrete wavelengths are measured at least one of which is between 1100 and 1300 nm and at least one of which is between 1590 and 1700 nm.

According to another embodiment, the discrete wavelength measurements are at 1150, 1195, 1215, 1230, 1240 and 1250 nm.

According to another embodiment, the discrete wavelength measurements are at 1595, 1610 and 1620 nm.

According to another embodiment, the discrete wavelength measurements are at 1150, 1195, 1215, 1230, 1240, and 1250 nm, and at 1595, 1610 and 1620 nm.

According to another embodiment, the subject is a human and the body part is a finger.

According to another embodiment, the constituent is glucose, and the tissue is blood.

According to another embodiment a second source of radiation is provided for discrete wavelengths.

BRIEF DESCRIPTION OF THE DRAWINGS

The invention will now be described in relation to the drawings in which.

DETAILED DESCRIPTION OF THE INVENTION

As used herein "concentration" or "concentration level" means the amount or quantity of a constituent in a solution whether the solution is in vitro or in vivo.

As used herein, "constituent" means a substance, or analyte found in a tissue and includes carbohydrates such as for example glucose, bilirubin, a protein, for examples albumin or, hemoglobin.

As used herein, "in a solution" means in a liquid environment such as, for examples interstitial, or other bodily fluid.

As used herein, "tissue" means any tissue of the body of a subject including for example, blood, extracellular spaces, and can mean the entire composition of a body part such as a finger or ear lobe.

As used herein "subject" means any member of the animal kingdom including, preferably, humans.

As discussed above, the present inventors have determined that in order to improve the ability to measure analytes in the tissue of a subject using a non-invasive device using spectral data, it is only necessary to add a limited number of discrete wavelength measurements in the longer wavelength NIR region to a full spectra absorption measurement at a continuum of wavelengths in the 500 to 1100 nm region to gain a significant improvement in analyte measurement accuracy. In particular analyte measurement accuracy achieved through previous methods is enhanced by adding a limited number of discrete wavelength measurements in the 1100 to 1300 nm (the "First region") and 1590 to 1700nm (the "Second region") region to a full spectra absorption measurement in the 500 to 1100 nm region to gain a significant improvement in analyte measurement accuracy. Preferably, wavelengths in the First region are 1150, 1195, 1215, 1230, 1240 and 1250 nm. A significant improvement can be made by adding only those wavelengths in the First region. Also adding wavelengths in the Second region, preferably 1595, 1610 and 1620 nm, can further enhance accuracy. However the high loss of light because of water absorption at the wavelengths in the Second region make measurement at these wavelengths more difficult. The method of the present invention provides for measurements of a body part to be taken in the AV and NIR region and added to measurements taken in either the First region or the First and Second regions. It will be readily appreciated that the method includes addition of measurements in all three regions and that the measurements may be taken simultaneously or sequentially.

Figure 1:
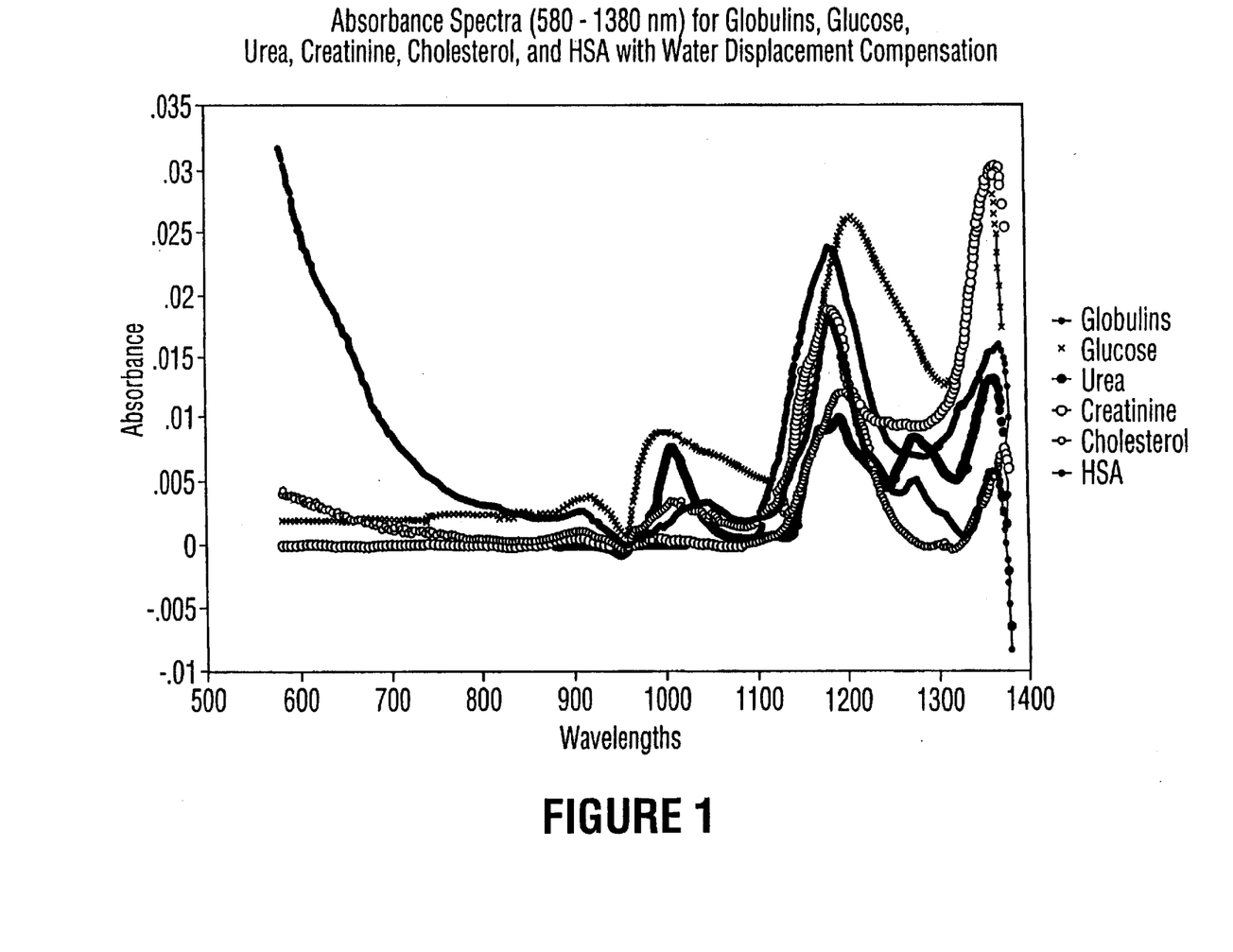
FIG. 1 shows absorbance spectra from 500–1380 nm for globulins, glucose, urea, creatine, cholesterol and human serum albumin with water displacement compensation.

The 580 to 1100 nm range has been used because, among other reasons, silicon detectors are sensitive in that range. Silicon detectors, particularly silicon-based detector arrays provide superior noise and dynamic range performance, are readily available, and, are relatively inexpensive. However, the 900 to 1700nm wavelength range provides sharper spectra for many of the analytes of interest as may be seen by referring to FIG. 1. An Indium Gallium Arsenite (InGaAs) detector arrays are typically used to measure spectra in this region. These provide inferior noise and dynamic range performance to silicon. Thus the lower signal to noise ratio offsets some of the advantage of the sharper spectra. Other detector arrays may also be used in these First and Second regions.

In one embodiment, to achieve a high signal to noise ratio for measurements at wavelengths in the First or Second regions, narrow band light is used to illuminate the tissue. Since the amount of light energy that can be delivered to the finger is limited by safety considerations, narrow band illumination allows a much higher intensity of light in a specific band, 10 nm for example, than can be utilized with a wideband source. This means that more light power for each wavelength can be delivered to the detector and thus makes it easier to achieve a high signal to noise ratio. As one skilled in the art will readily appreciate one approach would be to illuminate the finger sequentially at a high enough rate to sufficiently reduce errors from short term absorption changes in the finger due to the heart beat pulse and other effects. This approach is illustrated in FIG. 3.

Figure 3:
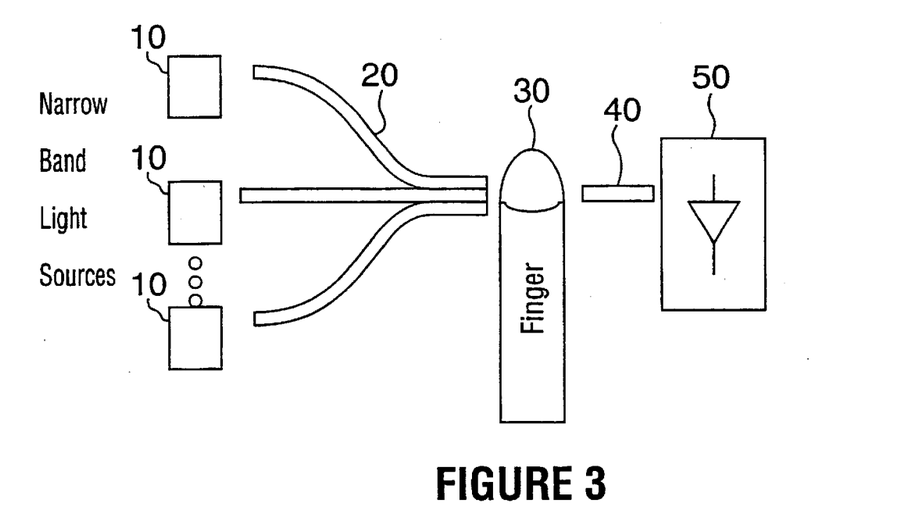
FIG. 3 is a diagram illustrating one embodiment of the present invention, multiple narrow band light sources, sequentially energized, and a single detector.

Referring to FIG. 3, the illumination sources (10) for a device of the invention can be any source of narrow band light with sufficient power, wavelength stability and consistency and amplitude stability. Examples of such devices are diode lasers, LEDs, LEDs with a filter associated with each LED to provide more narrow and tightly controlled bands, and photo luminescent material.

The light is delivered by a suitable conduit such as fibers (20) to the finger (30). The light emerging from the finger is collected and delivered to a single detector (50) using a fiber or other suitable conduit (40). For light of this wavelength an InGaAs photodiode is the preferred detector. As used herein, "light", "illumination", "radiation" all refer to the light energy provided by a source, or sources, that is capable of delivering sufficient light at each of the desired wavelengths.

Figure 4:
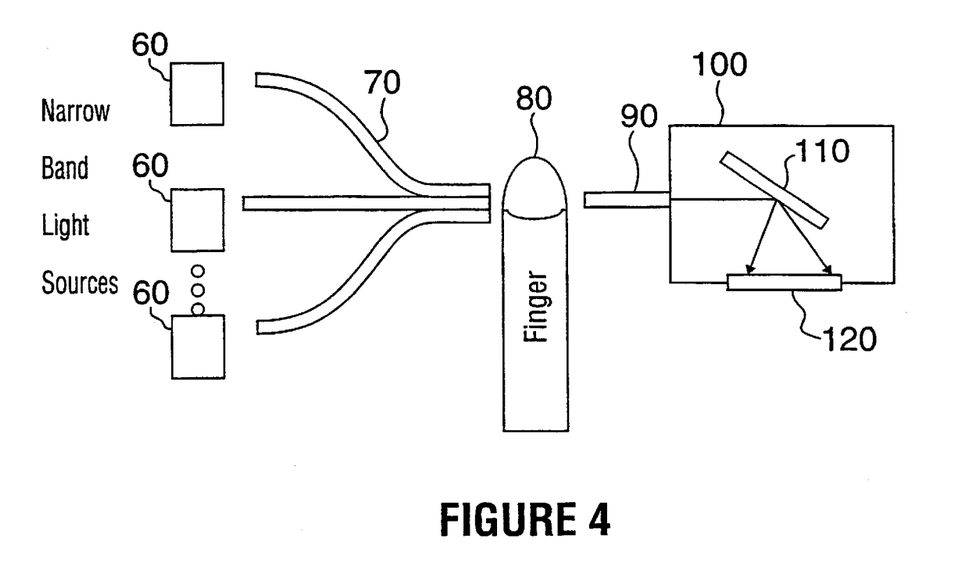
FIG. 4 is a diagram illustrating another embodiment of the present invention providing multiple narrow band light sources, simultaneously energized, and multiple detectors.

In another embodiment, the finger is illuminated with the above narrowband sources simultaneously. This is illustrated in FIG. 4. Light from multiple narrow band light sources (60) is delivered to the finger (80) by a suitable conduit (70). The collected light would be delivered to a spectrometer (100) by a conduit (90), separated into its individual wavelengths using a grating (110) and then delivered to individual detectors or a detector array (120). This approach reduces to some degree the light power per wavelength band that can be applied, but eliminates the error that exists in the first approach due to absorption changes in the finger which could effect each wavelength differently.

In a third embodiment, a light source which delivers continuous energy within the selected discrete wavelength range, for example 1100 to 1300 nm, is used to illuminate the finger. The collected light would be separated into its individual wavelengths using a grating and then delivered to individual detectors or a detector array. This approach may further reduce the light power per wavelength band that can be further applied, but it offers the advantage that the system's measurement accuracy is not dependent on the wavelength stability of the light source. The light source in this embodiment is described as being specific to the discrete wavelengths range. It is also possible to use for this purpose the same light source as is used to supply energy in the 500 to 1100 nm wavelength region. A further alternative is to use the same light source as used to supply energy in the 500 to 1100 nm wavelength region to supply energy to the discrete wavelength region and in addition boost the light intensity in the discrete wavelength region by a second source which supplies energy only in the discrete wavelength region.

With respect to the measurements in the AV and NIR region, the light source can emit light over a very wide band-width including light in the AV and NIR, for example a polychromatic source may be used. A light source which is specific to this region is preferred. According to one embodiment, the light from the light source passes first through a collimator, which is a collection of lenses that concentrate the light into a narrow parallel beam directed at the receptor. The receptor is shaped to receive within it that part of the subject being measured, for example, a finger or ear of a human. Alternatively, the receptor could be shaped so that the part of the human or animal, onto which the light is to be directed, is placed near the receptor rather than within the receptor. In any event, the body part is in contact with the receptor, and light is directed onto and is dispersed by the body part. The dispersed light is collected by lenses and directed through a slit to diffraction means. Alternatively, the means for collecting the light after it is directed onto a receptor are fibre optics that transmit said light to diffraction means. The collected light can be light that has passed through the body part or has reflected off the body part or a combination thereof. Preferably, the collected light is light that has passed through the parts of the subject.

The light from the grating disperses the light into its component wavelengths so that the light in the AV and NIR Eregion falls along the length of a linear array detector. As is understood, the array is comprised of individual detectors a range of which respond to the AV and NIR region. The array detector is electronically scanned by a microprocessor to measure intensity of light on each individual unit, or reflected from the tissue in the receptor. The detector is connected to a nicroprocessor, producing an output spectrum, with the microprocessor analyzing the measurements from the linear array detector and the individual InGaAs detectors ultimately producing a result for each concentration level determined. The results can be shown on a display and/or printed on a printer. A keyboard allows a user to control the device, for example, to specify a particular constituent to be measured. The timing and control may be activated by the microprocessor to control the device, for example, to determine number and timing of measurements.

The polychromatic light source can be a quartz-halogen or a tungsten-halogen bulb and is powered by a stabilized power source, for example, a DC power supply, or by a battery. Preferably, the linear array detector has at least ten elements, more preferably, 250–300 units for measurement over the AV and NIR region. A further advantage of a linear array detector is that it reduces the effect of pulses in the light signal waveform due to heartbeats because each diode is exposed to the pulsing light over exactly the same time interval.

After the measurements are taken for the transmittance and/or reflectance, the log of the inverse of these measurements is taken, that is, log 1/T and log 1/R, where T and R represent the transmittance and reflectance respectively. A reference set of measurements is taken of the incident light, being the light generated in the device when no part of the subject is in contact with the receptor. The absorbance is then calculated when a part of the subject, such as the finger, is in contact with the receptor as a ratio of measurements compared to the reference set of measurements.

Not be construed as a limitation on the method of the invention, optionally the second derivative of measurements may be taken in order to reduce any variation in the result that will be caused by a change in path length for the light.

The noise level within the device may be reduced by a multiple scanning technique whereby the linear array detector takes a number of measurements and then average the results. Preferably, the linear array detector and discrete longer wavelength detectors are scanned many times for several repetitions and then averages the results.

Known approaches to computation such as PLS and PCR may be used.

While measuring glucose concentrations is a preferred embodiment of the present invention, the device and method can be used to measure concentration levels of various other constituents found within the blood of humans and animals, for example, amino acids, nitrogen, blood oxygenation, carbon dioxide, cortisol, creatine, creatnine, glucose, ketones, lipids, fat, urea, amino acids, fatty acids, glycosylated hemoglobin, cholesterol, alcohol, lactate, $Ca^{++}$, $K^+$, $Cl_{-m}$ $HCO_{3-}$ and $HPO_{4-}$, to name a few. Indeed, as will be apparent to those skilled in the art, the method and device can be modified to measure several constituents simultaneously.

The following non-limiting examples are illustrative of the present invention:

EXAMPLES

Example 1

Simulator

A simulator has been developed to aid in the analysis of analyte measurement alternatives. It simulated all components of a system according to the present invention, namely light sources, light transmission means, optics, filters and detectors. It also simulated light loss through a body part based upon measured spectra of an analyte of interest as well as a number of interfering substances. The simulator developed combinations of body constituents on a random basis and then developed spectra of each combination. Examples of combinations developed are for example, for first set glucose 5 mM, total Hb 14 g/dL and $O_2$ Sat 95% etc.; sample No.2 glucose 7 mM; total Hb 13.5 g/dL and $O_2$ Sat 98%. It then calculated absorption values based upon these spectra as well as the instrument and detector characteristics such as noise, drift, factors that effect spectra, etc. The absorption measurements were then processed by the same algorithms routinely used in an instrument to calculate analyte predictions, such as that described above.

Using this simulator it was determined that two wavelength regions provide a surprisingly substantial improvement in glucose measurement accuracy when added to the 580 to 1100 nm measurements. These regions are 1100 to 1300 nm and 1590 to 1700 nm.

We have found that detection of a number of specific wavelength combinations provide significant improvement. According to a preferred embodiment the specific wavelengths are: 1150, 1195, 1215, 1230, 1240 and 1250nm in the First region and 1595, 1610 and 1620 nm in the Second region.

Since the improvement in glucose accuracy depends upon the accuracy with which these measurements can be made, noise and other errors were added to the absorption measurement by the simulator. A chart was developed that relates the improvement ratio (glucose error from 580 to 1100 nm measurements alone/glucose error from the combined measurement) to the error in absorption measurements. This relationship is shown on the attached FIG. 2. The improvement ratios in this chart were calculated based upon adding only the six wavelengths in the First region as defined above to the 580 to 1100 nm measurements.

Example 2

Feasibility Model

Figure 5:
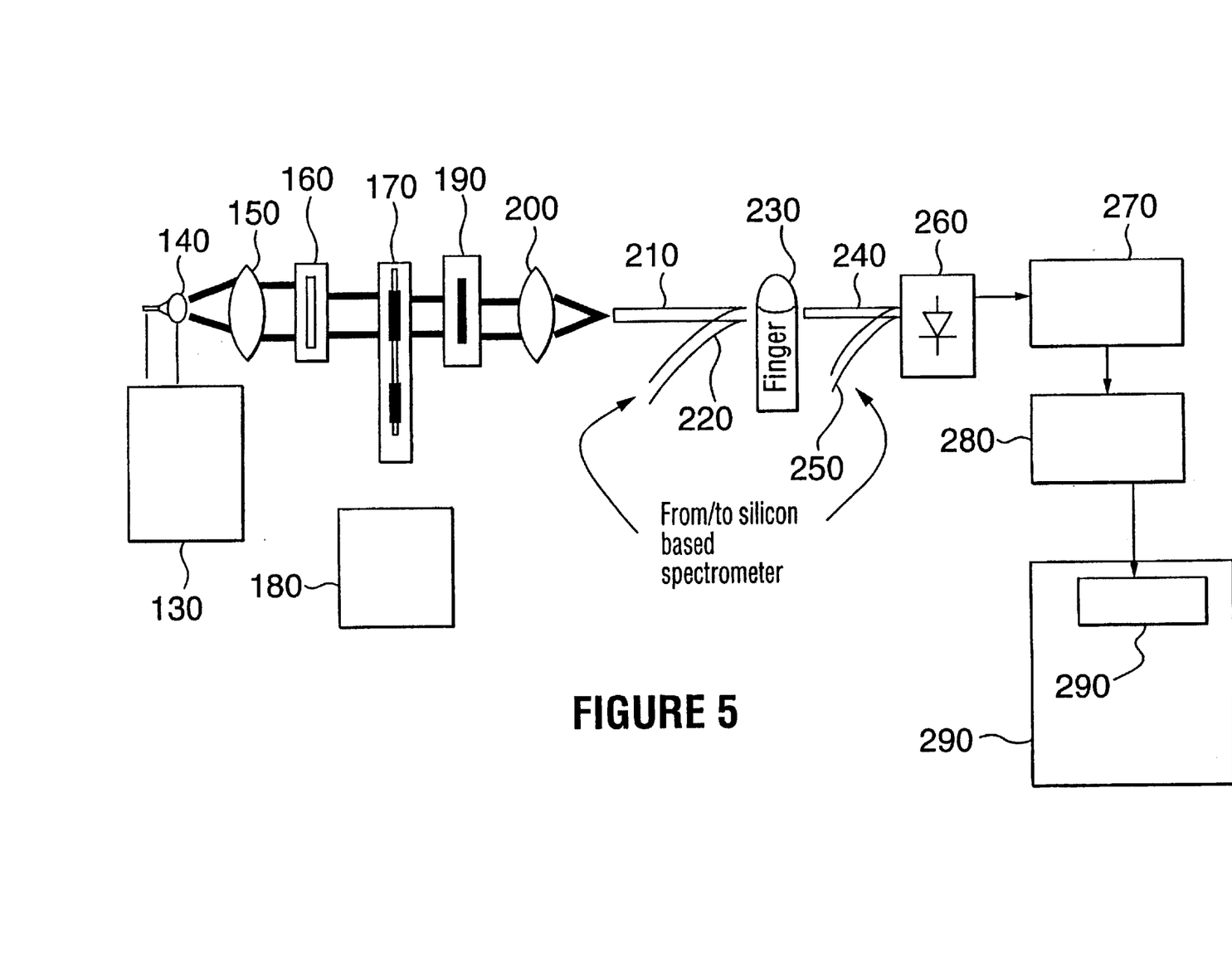
FIG. 5 is a diagram illustrating a further embodiment of the present invention which comprises a feasibility model of a system for determining the concentration of a constituent.

A feasibility model, as illustrated in FIG. 5, was built wherein the light source (140) consisted of a 100 watt tungsten halogen lamp assembly (Oriel QTH #60067) regulated by an intensity controller (Oriel 68850) (130) followed by a collimator (Oriel #60076) (150) and a shutter (Oriel#71446) (160). Individual wavelengths in the 1150 to 1250 nm region as defined in the preferred embodiment set out above are created by passing the light through interference filters with bandwidths of approximately 10 nm (Orion). Sequential illumination is achieved by mounting these filters onto a filter wheel (McPherson #941) (170) which is rotated by a Device Controller(McPherson #747) (180). As will be appreciated by those skilled in the art, other means are available to achieve delivery of discrete wavelengths in this range.

To further block stray light the light beam was passed through another bandpass filter (190) with a transmission range of 1140 to 1260nm(Orion). Light is delivered via a bifurcated fiber (210) to a finger receptor such as that described in U.S. Pat. No. 5,429, 128. Light passing through the finger (230) is delivered via a bifurcated fiber (240) to a cooled. InGaAs photodiode (Hamamatsu #G5832-13) (260). The current from the photodiode is amplified by current pre-amplifier and amplifier (Stanford Research #'s SR570 and SR560) (270 and 280). The resulting voltage is converted to a digital signal and input into a computer (300) via a Data Acquisition board (National Instruments AT-A1-16XE-10) (290).

The second legs of the illumination and collection bifurcated fibers (220 and 250) were used to connect a silicon based spectrometer that measured absorption in the 580 to 1100 nm region To date, noise and drift in the feasibility model have resulted in a range of absorption error of approximately 200 ∞OD, a level which our simulator predicted would result in an improvement ratio of 1.12. In spite of these errors, 2 diabetic volunteers were measured for a total of 3 days. During each day 16 spectra where taken over approximately 8 hours while each volunteer followed their normal course of eating and insulin injections. With each pair of spectral measurements, blood was drawn via a capillary tube from a finger stick and measured on a reference instrument (YSI). The data were processed for calibration using only the measurements in the 580 to 1100 nm region and using those referred to above for the First region. The results were:

| Wavelength region | SEC | % improvement | Ratio |
| --- | --- | --- | --- |
| 580 to 1100 nm | 1.86 | | |
| 580 to 1100 nm plus 1150 to 1250 | 1.23 | 34% | 1.17 |

Figure 2:
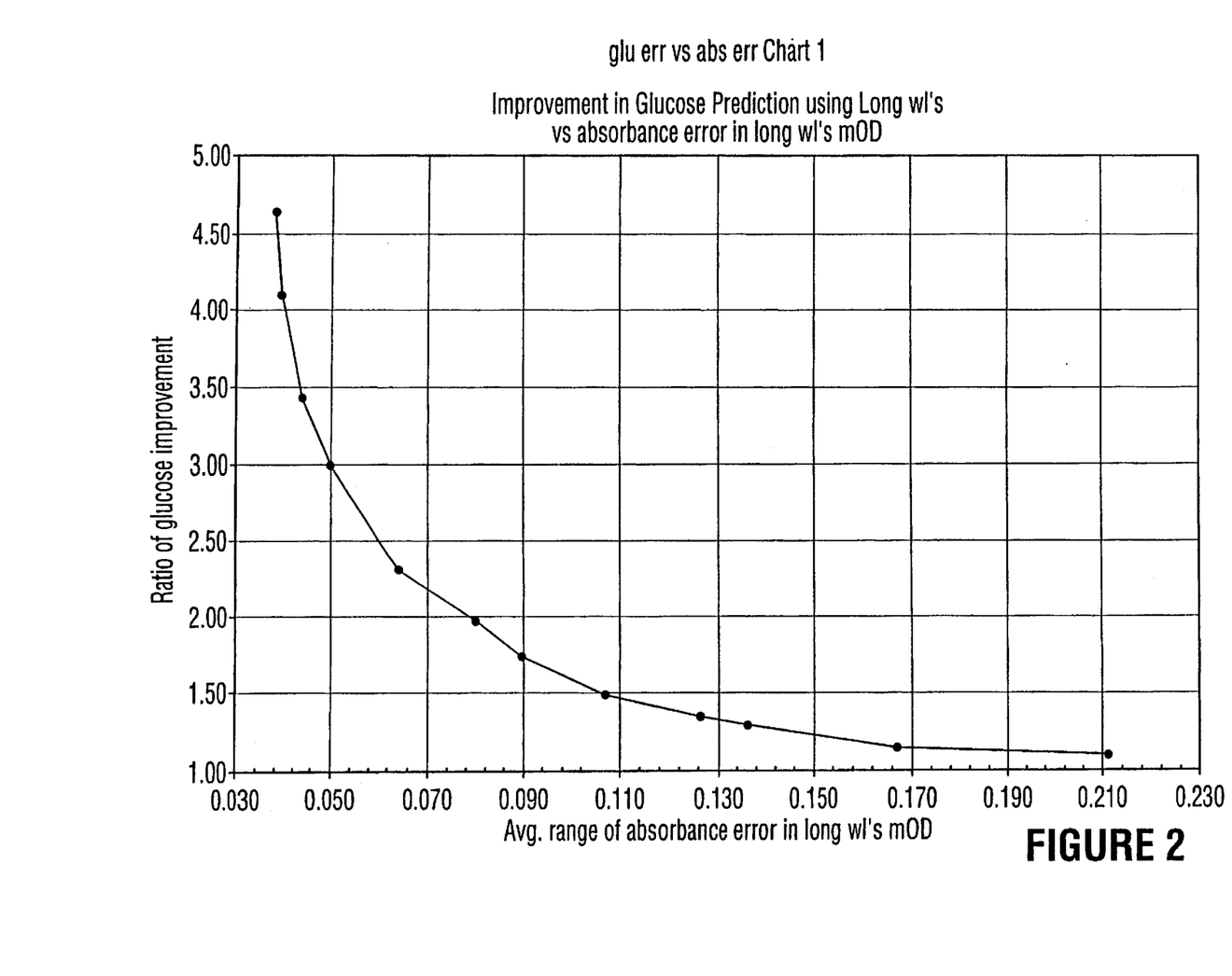
FIG. 2 is a graph showing improvement in glucose prediction in relation to absorbance error in the measurement at the discrete longer NIR wavelengths.

While this improvement is significant, it is appreciated that a much better improvement, and thus a lower glucose error, can be achieved by using a measurement configuration which produces a lower absorption measurement error, as is shown in FIG. 2.

While the present invention has been described with reference to what are presently considered to be preferred examples, it is to be understood that the invention is not limited to the disclosed examples. To the contrary, the invention is intended to cover various modifications and equivalents included within the spirit and scope of the appended claims.

All publications, patents and patent applications referred to herein are incorporated by reference in their entirety to the same extent as if each individual publication, patent or patent application was specifically and individually indicated to be incorporated by reference in its entirety.

We claim:

1. A method for determining a concentration of a constituent in a tissue of a subject comprising the steps of:

irradiating the tissue with a broad spectrum of radiation in the AV and NIR region from a first source of radiation;

irradiating the tissue with radiation in the longer wavelength NIR region from a second source of radiation;

measuring with a detector transmitted or radiation from the tissue at a continuum of wavelengths in the AV and NIR region and at one, or more than one discrete wavelength in the longer wavelength NIR region, wherein the continuum of wavelengths in the AV and NIR region is between 500 and 1100 nm, and wherein the one, or more than one discrete wavelength is between 1590 and 1700 nm; and calculating the concentration of the constituent on the basis of the measurements, thereby determining the concentration of the constituent in the tissue, wherein said first and second sources are approximately oppositely disposed to said detector.

2. A method according to claim 1, wherein the discrete wavelength measurements are at 1595, 1610 and 1620 nm.

3. A method according to claim 1 wherein the radiation at each discrete wavelength is provided by a separate energy source.

4. A method according to claim 1 wherein the radiation at each of the discrete wavelengths is provided sequentially.

5. A method according to claim 1 wherein the radiation at all of the discrete wavelengths is provided simultaneously.

6. A method according to claim 1 wherein a single energy source provides radiation in the range of 500 to 1300 nm.

7. A method according to claim 1 wherein the steps of irradiating the tissue in the AV and NIR region, and in the longer wavelength NIR region, are done simultaneously, and the measurement in each of said AV and NIR region and said longer wavelength NIR region is made simultaneously.

8. A method according to claim 1 wherein the subject is a human and the body part is a finger.

9. A method according to claim 1 wherein the constituent is glucose, and the tissue is blood.

10. A method for measuring concentration of a blood constituent within a body part of a living subject comprising:

irradiating a body part of the subject with a broad spectrum of radiation in the AV and NIR region from a first source of radiation;

collecting the radiation from the AV and NIR region after the radiation has been directed onto the part, wherein the collected radiation comprises a band of radiation from 500 to 1100 nm;

dispersing the collected radiation into a dispersed spectrum of component wavelengths onto a detector, the detector taking measurements transmitted and radiation from the collected radiation;

transferring the measurements to a processor;

irradiating the body part of the subject with radiation in the longer wavelength NIR region from a second source of radiation;

detecting with the detector one, or more than one discrete wavelength in the longer wavelength NIR region after the radiation has been directed onto the part, wherein the one, or more than one discrete wavelength is between 1590 and 1700 nm, the detector taking measurements of transmitted and reflected radiation; and transferring the measurements to a processor; based on the measurements and one or more calibration algorithms, the processor calculating the concentration of said constituent of said blood, wherein said first and second sources are approximately oppositely disposed to said detector.

11. The method according to claim 10 wherein the detector is a linear array detector and the measurement is of absorbed radiation.

12. A method according to claim 10, and wherein the discrete wavelength measurements are at 1595, 1610 and 1620 nm.

13. A method according to claim 10 wherein the subject is a human and the body part is a finger.

14. A method according to claim 10 wherein the constituent is glucose, and the tissue is blood.

15. A method for measuring concentration of a blood constituent within a body part of a living subject comprising:

irradiating the body part of the subject with a first continuum of a broad spectrum band of radiation in the AV and NIR region from a first source of radiation;

collecting the first band of radiation after the radiation has been directed onto the part, wherein the first band of radiation collected is between 500 and 1100 nm;

dispersing the continuum of collected radiation into a dispersed spectrum of component wavelengths onto a detector, the detector taking measurements of transmitted and radiation from the collected radiation; and transferring the measurements to a processor;

irradiating the body part of the subject with a second continuum of a radiation band in the longer wave NIR region from a second source of radiation;

collecting the second band of radiation after the radiation has been directed onto the part;

dispersing the continuum of collected radiation into a dispersed spectrum of component wavelengths onto the detector;

detecting with the detector one, or more than one discrete wavelengths in the longer wavelength NIR region with the detector, wherein the one, or more than one discrete wavelength is between 1590 and 1700 nm, the detector taking measurements of transmitted and radiation from the collected radiation; and transferring the measurements to a processor based on the measurements and one or more calibration algorithms, the processor calculating the concentration of said constituent of said blood, wherein said first and second sources are approximately oppositely disposed to said detector.

16. The method according to claim 15 wherein the detector is a linear array detector and the measurement is of absorbed radiation.

17. A method according to claim 15, wherein the discrete wavelength measurements are at 1595, 1610 and 1620 nm.

18. The method according to claim 15 wherein the subject is a human and the body part is a finger.

19. A method according to claim 15 wherein the constituent is glucose, and the tissue is blood.

20. A method for determining a concentration of a constituent in a tissue of a subject comprising the steps of:
irradiating the tissue with a broad spectrum of radiation in the AV and NIR region from a first source of radiation;
irradiating the tissue with radiation in the longer wavelength NIR region from a second source of radiation,
measuring with a detector transmitted or radiation from the tissue at a continuum of wavelengths in the AV and NIR region, at one, or more than one discrete wavelength between 1100 and 1300 nm, and at one, or more than one discrete wavelength between 1590 and 1700 nm, wherein the continuum of wavelengths in the AV and NIR region is between 500 and 1100 nm; and
calculating the concentration of the constituent on the basis of the measurements, thereby determining the concentration of the constituent in the tissue, wherein the first and second sources are approximately oppositely disposed to said detector.

21. A method according to claim 20, wherein the discrete wavelength measurements are at 1150, 1195, 1215, 1230, 1240, and 1250 nm, and at 1595, 1610 and 1620 nm.

22. A method according to claim 20, wherein the radiation at each discrete wavelength is provided by a separate energy source.

23. A method according to claim 20, wherein the radiation at each of the discrete wavelengths is provided sequentially.

24. A method according to claim 20, wherein the radiation at all of the discrete wavelengths is provided simultaneously.

25. A method according to claim 20, wherein a single energy source provides continuous energy over the radiation range of 1100 to 1300 nm.

26. A method according to claim 20, wherein the steps of irradiating the tissue in the AV and NIR region, and in the longer wavelength NIR region, are done simultaneously, and the measurement in each of said AV and NIR region and said longer wavelength NIR region is made simultaneously.

27. The method according to claim 20, wherein the subject is a human and the body part is a finger.

28. A method according to claim 20, wherein the constituent is glucose, and the tissue is blood.

29. A method for measuring concentration of a blood constituent within a body part of a living subject comprising:
irradiating a body part of the subject with a broad spectrum of radiation in the AV and NIR region from a first source of radiation;
collecting the radiation from the AV and NIR region after the radiation has been directed onto the part, wherein the collected radiation comprises a band of radiation between 500 and 1100 nm;
dispersing the collected radiation into a dispersed spectrum of component wavelengths onto a detector, the detector taking measurements of transmitted and radiation from the collected radiation;
transferring the measurements to a processor;
irradiating the body part of the subject with radiation in the longer wavelength NIR region from a second source of radiation;
detecting with the detector one, or more than one discrete wavelength between 1100 and 1300 nm, and one, or more than one discrete wavelength between 1590 and 1700 nm with a detector, the detector taking measurements of transmitted and radiation; and
transferring the measurements to a processor; based on the measurements and one or more calibration algorithms, the processor calculating the concentration of said constituent of said blood,
wherein the first and second sources are approximately oppositely disposed to said detector.

30. The method according to claim 29, wherein the detector is a linear array detector and the measurement is of absorbed radiation.

31. A method according to claim 29, wherein the discrete wavelength measurements are at 1150, 1195, 1215, 1230, 1240, and 1250 nm, and at 1595, 1610 and 1620 nm.

32. The method according to claim 29, wherein the subject is a human and the body part is a finger.

33. A method according to claim 29, wherein the constituent is glucose, and the tissue is blood.

34. A method for measuring concentration of a blood constituent within a body part of a living subject comprising:
irradiating the body part of the subject with a first continuum of a broad spectrum band of radiation in the AV and NIR region from a first source of radiation;
collecting the first band of radiation after the radiation has been directed onto the part, wherein the first band of radiation collected is between 500 and 1100 nm;
dispersing the continuum of collected radiation into a dispersed spectrum of component wavelengths onto a detector, the detector taking measurements transmitted and radiation from the collected radiation; and
transferring the measurements to a processor;
irradiating the body part of the subject with a second continuum of a radiation band in the longer wave NIR region from a second source of radiation;
collecting the second band of radiation after the radiation has been directed onto the part;
dispersing the continuum of collected radiation into a dispersed spectrum of component wavelengths onto the detector;
detecting with the detector one, or more than one discrete wavelength between 1100 and 1300 nm, and one, or more than one discrete wavelength between 1590 and 1700 nm with a detector, the detector taking measurements of transmitted and radiation; and
transferring the measurements to a processor based on the measurements and one or more calibration algorithms, the processor calculating the concentration of said constituent of said blood,
wherein said first and second sources are approximately oppositely disposed to said detector.

35. The method according to claim 34, wherein the detector is a linear array detector and the measurement is of absorbed radiation.

36. A method according to claim 34, wherein the discrete wavelength measurements are at 1150, 1195, 1215, 1230, 1240, and 1250 nm, and at 1595, 1610 and 1620 nm.

37. The method according to claim 34, wherein the subject is a human and the body part is a finger.

38. A method according to claim 34, wherein the constituent is glucose, and the tissue is blood.

* * * * *

UNITED STATES PATENT AND TRADEMARK OFFICE
CERTIFICATE OF CORRECTION

PATENT NO. : 6,741,876 B1
DATED : May 25, 2004
INVENTOR(S) : Thomas Scecina, Romuald Pawluczyk and Theodore E. Cadell It is certified that error appears in the above-identified patent and that said Letters Patent is hereby corrected as shown below:

Title page,
Item [75], Inventors, delete the name "Romauld" and substitute therefore
-- Romuald --.

Signed and Sealed this

Third Day of August, 2004

JON W. DUDAS
*Acting Director of the United States Patent and Trademark Office*

UNITED STATES PATENT AND TRADEMARK OFFICE
CERTIFICATE OF CORRECTION

PATENT NO. : 6,741,876 B1
DATED : May 25, 2004
INVENTOR(S) : Thomas Scecina, Romuald Pawluczyk and Theodore E. Cadall It is certified that error appears in the above-identified patent and that said Letters Patent is hereby corrected as shown below:

Column 11,
Line 22, "transmitted or radiation from" should read -- radiation transmitted through --.
Line 66, "transmitted and radiation from" should read -- of transmitted radiation --.

Column 12,
Line 10, "and reflected" should be deleted.
Line 38, the first occurrence of "and" should be deleted.
Line 49, "wavelengths" should read -- wavelength --.
Lines 49-50, "with the detector" should be deleted --.
Line 52, "and" should be deleted.
Line 54, insert a -- ; -- after "processor".

Column 13,
Line 9, "transmitted or radiation from" should read -- radiation transmitted through --.
Line 54, "and" should be deleted.

Column 14,
Lines 2 and 44, the first occurrence of "and" should be deleted.
Lines 29-30, "transmitted and radiation" should read -- of transmitted radiation --.
Line 43, "with a detector" should be deleted.

Signed and Sealed this

Twenty-first Day of February, 2006

JON W. DUDAS
*Director of the United States Patent and Trademark Office*